United States Patent [19]
Macina et al.

[11] Patent Number: 5,874,243
[45] Date of Patent: Feb. 23, 1999

[54] OLRCC15 RECEPTOR

[75] Inventors: Roberto Anibal Macina, Drexil Hill; Ganesh Madhusudan Sathe, King of Prussia, both of Pa.

[73] Assignee: SmithKline Beecham Corporation, Philadelphia, Pa.

[21] Appl. No.: 827,291

[22] Filed: Mar. 28, 1997

[51] Int. Cl.$^6$ ..................................... C12N 15/00
[52] U.S. Cl. ..................... 435/69.1; 435/325; 435/320.1; 435/71.1; 536/23.5; 536/23.1; 530/350
[58] Field of Search .................... 435/69.1, 325, 435/320.1, 71.1; 536/23.5, 23.1; 530/350

[56] References Cited

PUBLICATIONS

Hillier et al., The WashU–Merck EST Project, Genbank accession No. AA042813, Sep. 1996.
George et al., Macromolecular sequencing and synthesis, Alan Riss , pp. 127–149, 1988.
EST 961576.
EST 961584.
Accession L34074.
Accession M84005.
Accession U50948.
Nef et al., "Spatial pattern of receptor expression in the olfactory epithelium", Proc. Natl. Acad. Sci. USA, vol. 89, pp. 8948–8952, Oct. 1992.
Thomas et al., "Chemoreceptors expressed in taste, olfactory and male reproductive tissue", Gene, vol. 178, pp. 1–5, (1996).
Parmentier et al., "Expression of members of the putative olfactory receptory gene family in mammalian germ cells", Nature, vol. 355, pp. 453–455, Jan. 1992.
Vanderhaeghen et al, "Specific Repertoire of Olfactory Receptor Genes in the Male Germ Cells of Several Mammalian Species", Genomics, vol. 39, pp. 239–246 (1997).
Drutel et al., "Cloning of OL1, a Putative Olfactory Receptor and its Expression in the Developing Rat Heart", Receptors and Channels, vol. 3, pp. 33–40 (1995).

*Primary Examiner*—Lila Feisee
*Assistant Examiner*—Eliane Lazar-Wesley
*Attorney, Agent, or Firm*—Ratner & Prestia; William T. King; William T. Han

[57] ABSTRACT

OLRCC15 receptor polypeptides and polynucleotides and methods for producing such polypeptides by recombinant techniques are disclosed. Also disclosed are methods for utilizing OLRCC15 receptor polypeptides and polynucleotides in the design of protocols for the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

27 Claims, 2 Drawing Sheets

| | | |
|---|---|---|
| 1 | AAAAAACTCCATCCATTATTTATTAGATACTATAATTCTAATTTTTCAATGGAGAAAGGG | 60 |
| 61 | GATGCTCAGAAGAAAACCTTAGGACAAGCTCTATAATTTCGTGAGACAGTGTTGAAAGAA | 120 |
| 121 | CATATTTCGTTCAGATTCTATATTTCTTGACCTTTTAGTTTCCTACTTCTATTCATGCTG | 180 |
| 181 | TATTGATCACCCAACTACAGAAGTTACCACAATCACATGATTTATAAGGCACTGAGTAAA | 240 |
| 241 | GTTTTACCAAATTAATACGCTGGTTTTGTGGTACTAGGTAAAAAGCATACACATCATGGC | 300 |
| |                                                                    M  A | |
| 301 | AAGGGAGAATTCGACCTTCAACTCCGACTTCATCTTCCTGGGAATCTTCAATCACAGCCC | 360 |
| |     R  E  N  S   T   F   N  S  D   F   I   F   L   G   I   F  N  H  S   P | |
| 361 | CACCCACACCTTCCTCTTCTTTCTGGTCCTGGCCATCTTTTCAGTGGCCTTCATGGGAAA | 420 |
| |     T   H   T   F   L   F   F   L   V  L  A   I   F   S   V  A   F   M  G  N | |
| 421 | CTCTGTCATGGTTCTCCTCATCTACCTGGACACCCAGCTCCACACCCCCATGTACCTCCT | 480 |
| |     S   V   M  V  L   L   I   Y   L   D   T   Q   L   H   T   P   M  Y   L   L | |
| 481 | CCTCAGCCAACTGTCCCTCATGGACCTCATGCTCATCTGCACCACCGTACCCAAGATGGC | 540 |
| |     L   S   Q  L   S   L   M  D  L   M   L   I   C   T   T   V   P   K   M  A | |
| 541 | CTTCAACTACCTGTCTGGCAGCAAGTCCATTTCTATGGCTGGTTGTGCCACACAAATTTT | 600 |
| |     F   N  Y   L   S   G   S   K   S   I   S   M  A  G   C   A   T   Q   I   F | |
| 601 | CTTCTATACATCACTGCTTGGCTCTGAATGCTTTCTTTTGGCTGTTATGGCTTATGACCG | 660 |
| |     F   Y   T   S   L   L   G   S   E   C   F   L   L  A   V   M  A  Y   D   R | |
| 661 | CTACACTGCCATTTGCCACCCTCTAAGATACACCAATCTCATGAGCCCTAAAATTTGTGG | 720 |
| |     Y   T   A   I   C   H   P   L   R   Y   T   N   L   M   S   P   K   I   C   G | |
| 721 | ACTTATGACTGCCTTTTCCTGGATCCTGGGCTCTACAGATGGAATCATTTATGCTGTAGC | 780 |
| |     L   M   T   A   F   S   W   I   L   G   S   T   D   G   I   I   Y   A   V   A | |

FIG. 1A

```
781  CACATTTTCCTTCTCCTACTGTGGGTCTCGGGAAATAGCCCACTTCTTCTGTGAGTTACC  840
      T  F  S  F  S  Y  C  G  S  R  E  I  A  H  F  F  C  E  L  P

841  TTCCCTACTAATCCTCTCATGCAATGACACATCAATATTTGAAAAGGTTATTTTCATTTG  900
      S  L  L  I  L  S  C  N  D  T  S  I  F  E  K  V  I  F  I  C

901  CTCTATAGTAATGCTTGTTTTCCCTGTTGCAATCATCATTGCTTCCTATGCTGGAGTTAT  960
      S  I  V  M  L  V  F  P  V  A  I  I  I  A  S  Y  A  G  V  I

961  TCTGGCTGTCATTCACATGGGATCTGGAGAGGGTCGTCGCAAAGCTTTCACGACCTGTTC  1020
      L  A  V  I  H  M  G  S  G  E  G  R  R  K  A  F  T  T  C  S

1021 CTCTCACCTCATGGTGGTGGGAATGTTCTATGGAGCAGGTTTGTTCATGTACATACAGCC  1080
      S  H  L  M  V  V  G  M  F  Y  G  A  G  L  F  M  Y  I  Q  P

1081 CACATCTGATCGCTCCCCAACGCAGGACAAGCTGGTGTCTGTATTCTACACCATCCTCAC  1140
      T  S  D  R  S  P  T  Q  D  K  L  V  S  V  F  Y  T  I  L  T

1141 TCCCATGCTGAATCCCCTCATCTACAGCCTCCGCAACAAGGAAGTGACCAGAGCATTCAT  1200
      P  M  L  N  P  L  I  Y  S  L  R  N  K  E  V  T  R  A  F  M

1201 GAAGATCTCAGGAAAGGGCAAGTCTGGAGAGAGAGTTACCTCATAAACTTTATGTTTTGA  1260
      K  I  S  G  K  G  K  S  G  E  R  V  T  S

1261 TGTCTGCTAAATTATTCTCTTCTAATATCC  1290
```

FIG. 1B

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1290 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
AAAAAACTCC ATCCATTATT TATTAGATAC TATAATTCTA ATTTTTCAAT GGAGAAAGGG        60
GATGCTCAGA AGAAAACCTT AGGACAAGCT CTATAATTTC GTGAGACAGT GTTGAAAGAA       120
CATATTTCGT TCAGATTCTA TATTTCTTGA CCTTTTAGTT TCCTACTTCT ATTCATGCTG       180
TATTGATCAC CCAACTACAG AAGTTACCAC AATCACATGA TTTATAAGGC ACTGAGTAAA       240
GTTTTACCAA ATTAATACGC TGGTTTTGTG GTACTAGGTA AAAAGCATAC ACATCATGGC       300
AAGGGAGAAT TCGACCTTCA ACTCCGACTT CATCTTCCTG GGAATCTTCA ATCACAGCCC       360
CACCCACACC TTCCTCTTCT TTCTGGTCCT GGCCATCTTT TCAGTGGCCT TCATGGGAAA       420
CTCTGTCATG GTTCTCCTCA TCTACCTGGA CACCCAGCTC CACACCCCA TGTACCTCCT       480
CCTCAGCCAA CTGTCCCTCA TGGACCTCAT GCTCATCTGC ACCACCGTAC CAAGATGGC       540
CTTCAACTAC CTGTCTGGCA GCAAGTCCAT TTCTATGGCT GGTTGTGCCA CACAAATTTT       600
CTTCTATACA TCACTGCTTG GCTCTGAATG CTTTCTTTTG GCTGTTATGG CTTATGACCG       660
CTACACTGCC ATTTGCCACC CTCTAAGATA CACCAATCTC ATGAGCCCTA AAATTTGTGG       720
ACTTATGACT GCCTTTTCCT GGATCCTGGG CTCTACAGAT GGAATCATTT ATGCTGTAGC       780
CACATTTTCC TTCTCCTACT GTGGGTCTCG GGAAATAGCC CACTTCTTCT GTGAGTTACC       840
TTCCCTACTA ATCCTCTCAT GCAATGACAC ATCAATATTT GAAAAGGTTA TTTTCATTTG       900
CTCTATAGTA ATGCTTGTTT TCCCTGTTGC AATCATCATT GCTTCCTATG CTGGAGTTAT       960
TCTGGCTGTC ATTCACATGG GATCTGGAGA GGGTCGTCGC AAAGCTTTCA CGACCTGTTC      1020
CTCTCACCTC ATGGTGGTGG GAATGTTCTA TGGAGCAGGT TTGTTCATGT ACATACAGCC      1080
CACATCTGAT CGCTCCCCAA CGCAGGACAA GCTGGTGTCT GTATTCTACA CCATCCTCAC      1140
TCCCATGCTG AATCCCCTCA TCTACAGCCT CCGCAACAAG GAAGTGACCA GAGCATTCAT      1200
GAAGATCTCA GGAAAGGGCA AGTCTGGAGA GAGAGTTACC TCATAAACTT TATGTTTTGA      1260
TGTCTGCTAA ATTATTCTCT TCTAATATCC                                       1290
```

( 2 ) INFORMATION FOR SEQ ID NO:2:

( i ) SEQUENCE CHARACTERISTICS:
        ( A ) LENGTH: 316 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ala Arg Glu Asn Ser Thr Phe Asn Ser Asp Phe Ile Phe Leu Gly
 1               5                  10                  15

Ile Phe Asn His Ser Pro Thr His Thr Phe Leu Phe Leu Val Leu
                20                  25                  30

Ala Ile Phe Ser Val Ala Phe Met Gly Asn Ser Val Met Val Leu Leu
                35                  40                  45

Ile Tyr Leu Asp Thr Gln Leu His Thr Pro Met Tyr Leu Leu Leu Ser
         50                  55                  60

Gln Leu Ser Leu Met Asp Leu Met Leu Ile Cys Thr Thr Val Pro Lys
65                  70                  75                  80

Met Ala Phe Asn Tyr Leu Ser Gly Ser Lys Ser Ile Ser Met Ala Gly
                85                  90                  95

Cys Ala Thr Gln Ile Phe Phe Tyr Thr Ser Leu Leu Gly Ser Glu Cys
               100                 105                 110

Phe Leu Leu Ala Val Met Ala Tyr Asp Arg Tyr Thr Ala Ile Cys His
               115                 120                 125
```

| | | | | | | | | | | | | | | |
|---|---|---|---|---|---|---|---|---|---|---|---|---|---|---|
| Pro | Leu 130 | Arg | Tyr | Thr | Asn | Leu 135 | Met | Ser | Pro | Lys | Ile 140 | Cys | Gly | Leu | Met |
| Thr 145 | Ala | Phe | Ser | Trp | Ile 150 | Leu | Gly | Ser | Thr | Asp 155 | Gly | Ile | Ile | Tyr | Ala 160 |
| Val | Ala | Thr | Phe | Ser 165 | Phe | Ser | Tyr | Cys | Gly 170 | Ser | Arg | Glu | Ile | Ala 175 | His |
| Phe | Phe | Cys | Glu 180 | Leu | Pro | Ser | Leu | Leu 185 | Ile | Leu | Ser | Cys | Asn 190 | Asp | Thr |
| Ser | Ile | Phe 195 | Glu | Lys | Val | Ile | Phe 200 | Ile | Cys | Ser | Ile | Val 205 | Met | Leu | Val |
| Phe | Pro 210 | Val | Ala | Ile | Ile | Ile 215 | Ala | Ser | Tyr | Ala | Gly 220 | Val | Ile | Leu | Ala |
| Val 225 | Ile | His | Met | Gly | Ser 230 | Gly | Glu | Gly | Arg | Arg 235 | Lys | Ala | Phe | Thr | Thr 240 |
| Cys | Ser | Ser | His | Leu 245 | Met | Val | Val | Gly | Met 250 | Phe | Tyr | Gly | Ala | Gly 255 | Leu |
| Phe | Met | Tyr | Ile 260 | Gln | Pro | Thr | Ser | Asp 265 | Arg | Ser | Pro | Thr | Gln 270 | Asp | Lys |
| Leu | Val | Ser 275 | Val | Phe | Tyr | Thr | Ile 280 | Leu | Thr | Pro | Met | Leu 285 | Asn | Pro | Leu |
| Ile | Tyr 290 | Ser | Leu | Arg | Asn | Lys 295 | Glu | Val | Thr | Arg | Ala 300 | Phe | Met | Lys | Ile |
| Ser 305 | Gly | Lys | Gly | Lys | Ser 310 | Gly | Glu | Arg | Val | Thr 315 | Ser | | | | |

OLRCC15 RECEPTOR

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to an olfactory receptor of the 7-transmembrane receptor family, hereinafter referred to as the OLRCC15 receptor. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). These proteins are herein referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors (otherwise known as 7-transmembrane (7 TM) receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 TM regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 TM receptors have been successfully introduced onto the market.

This indicates that these receptors have an established, proven history as therapeutic targets. Clearly, there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to OLRCC15 receptor polypeptides and recombinant materials and methods for their production. Another aspect of the invention relates to methods for using such OLRCC15 receptor polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with OLRCC15 receptor imbalance with the identified compounds. Yet another aspect of the invention relates to diagnostic assays for detecting diseases associated with inappropriate OLRCC15 receptor activity or levels.

BRIEF DESCRIPTION OF THE DRAWINGS

FIG. 1 shows the nucleotide and deduced amino acid sequence from a Human OLRCC15 receptor (SEQ ID NOS: 1 and 2).

DESCRIPTION OF THE INVENTION

Definitions

The following definitions are provided to facilitate understanding of certain terms used frequently herein.

"OLRCC15 receptor" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said OLRCC15 receptor including similar activities or improved activities or these activities with decreased undesirable side-effects. Also included are antigenic and immunogenic activities of said OLRCC15 receptor.

"OLRCC15 receptor gene" refers to a polynucleotide comprising the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS-STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec* Biol (1990) 215:403).

Polypeptides of the Invention

In one aspect, the present invention relates to OLRCC15 receptor polypeptides. The polypeptides include the polypeptide of SEQ ID NO:2; as well aspolypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Also included within OLRCC15 receptor polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Preferably, OLRCC15 receptor polypeptides exhibit at least one biological activity of the receptor.

The OLRCC15 receptor polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the OLRCC15 receptor polypeptides are also included in the invention. A fragment is a polypeptide having an amino acid sequence that entirely is the same as part, but not all, of the amino acid sequence of the aforementioned OLRCC15 receptor polypeptides. As with OLRCC15 receptor polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of OLRCC15 receptor polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of OLRCC15 receptor polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The OLRCC15 receptor polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to OLRCC 15 receptor polynucleotides. OLRCC15 receptor polynucleotides include isolated polynucleotides which encode the OLRCC15 receptor polypeptides and fragments, and polynucleotides closely related thereto. More specifically, OLRCC15 receptor polynucleotide of the invention include a polynucleotide comprising the nucleotide sequence set forth in SEQ ID NO:1 encoding a OLRCC15 receptor polypeptide of SEQ ID NO: 2, and polynucleotide having the particular sequence of SEQ ID NO:1. OLRCC15 receptor polynucleotides further include a polynucleotide comprising a nucleotide sequence that has at least 80% identity to a nucleotide sequence encoding the OLRCC15 receptor polypeptide of SEQ ID NO:2 over its entire length, and a polynucleotide that is at least 80% identical to that having SEQ ID NO:1 over its enire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under OLRCC15 receptor polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such OLRCC15 receptor polynucleotides.

OLRCC15 receptor of the invention is structurally related to other proteins of the olfactory receptor, as shown by the results of sequencing the cDNA encoding human OLRCC15 receptor. The cDNA sequence contains an open reading frame encoding a polypeptide of 316 amino acids. Amino acid sequence of FIG. 1 (SEQ ID NO:2) has about 44.7% identity (using TFASTA) in 304 amino acid residues with odorant receptor (G. Drutel, J. M. Arrang, J. Diaz, C. Wisnewsky, K. Schwartz & J. C. Schwartz (1995), Cloning of OL1, a putative olfactory receptor and its expression in the developing rat heart, Recept. Channels 3, 33–40). Furthermore, the amino acid sequence of OLRCC15 (SEQ ID NO:2) is 41.0% identical to mouse G-protein coupled receptor, olfactory receptor over 312 amino acid residues (P. Nef, I. Hermans-Borgmeyer, H. Artieres-Pin, L. L. Beasley, V. E. Dionne & S. F. Heinemann (1992), Spatial pattern of receptor expression in the olfactory epithelium, Proc. Natl. Acad. Sci. U.S.A. 89: 8948–8952). Nucleotide sequence of FIG. 1 (SEQ ID NO:1) has about 67.82% identity (using BlastN) in 463 nucleotide residues with *H. sapiens* mRNA for TPCR100 protein (Vanderhaeghen, P., Schurmans, S., Vassart, G. and Parmentier, M. Male germ cells from several mammalian species express a specific repertoire of olfactory receptor genes. GeneBank ACCESSION X89666. Submitted (12-Jul.-1995) P. Vanderhaeghen, Universit Libre de Bruxelles, IRIBHN, ULB Campus Erasme, 808 route de Lennik, 1070 Bruxelles, BELGIUM). Furthermore, OLRCC15 (SEQ ID NO:1) is 55.94% identical to *H. sapiens* HGMP07I gene for olfactory receptor over 935 nucleotide base residues (M. Parmentier, F. Libert, S. Schurmans, S. Schiffmann, A. Lefort, D. Eggerickx, C. Ledent, C. Mollereau, C. Gerard, J. Perret, J. A. Grootegoed & G. Vassart (1992), Expression of members of the putative olfactory receptor gene family in mammalian germ cells, Nature 355, 453–455).

One polynucleotide of the present invention encoding OLRCC15 receptor may be obtained using standard cloning and screening, from a cDNA library derived from mRNA in cells of human colon and human blood using the expressed sequence tag (EST) analysis (Adams, M.D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding OLRCC15 receptor polypeptide of SEQ ID NO:2 may be identical over its entire length to the coding sequence set forth in FIG. 1 (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention comprise a nucleotide sequence that is highly identical, at least 80% identical, with a nucleotide sequence encoding a OLRCC15 receptor polypeptide, or at least 80% identical with the sequence contained in FIG. 1 (SEQ ID NO: 1) encoding OLRCC15 receptor polypeptide, or at least 80% identical to a nucleotide sequence encoding the polypeptide of SEQ ID NO:2.

When the polynucleotides of the invention are used for the recombinant production of OLRCC15 receptor polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding OLRCC15 receptor variants comprising the amino acid sequence of OLRCC 15 receptor polypeptide of FIG. 1 (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO:1, may be used as hybridization probes for cDNA and genomic DNA, to isolate full-length cDNAs and genomic clones encoding OLRCC15 receptor and to isolate cDNA and genomic clones of other genes that have a high sequence similarity to the OLRCC15 receptor gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding an olfactory receptor comprises the steps of screening an appropriate library under stingent hybridization conditions with a labeled probe having the SEQ ID NO: 1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989), such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the OLRCC15 receptor polypeptide is to be expressed for use in screening assays, generally, it is preferred that the polypeptide be produced at the surface of the cell. In this event, the cells may be harvested prior to use in the screening assay. If OLRCC15 receptor polypeptide is secreted into the medium, the medium can be recovered in order to recover and purify the polypeptide; if produced intracellularly, the cells must first be lysed before the polypeptide is recovered.

OLRCC15 receptor polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of OLRCC15 receptor polynucleotides for use as diagnostic reagents. Detection of a mutated form of OLRCC15 receptor gene associated with a dysfunction will provide a diagnostic tool that can add to or define a diagnosis of a disease or susceptibility to a disease which results from under-expression, over-expression or altered expression of OLRCC15 receptor. Individuals carrying mutations in the OLRCC15 receptor gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled OLRCC15 receptor nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85: 4397–4401. In another embodiment, an array of oligonucleotides probes comprising OLRCC15 receptor nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the OLRCC15 receptor gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of OLRCC15 receptor polypeptide or OLRCC15 receptor mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an OLRCC 15 receptor, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the OLRCC15 receptor polypeptides. The term "immunospecific" means that the antibodies have substantial greater affinity for the polypeptides of the invention than their affinity for other related polypeptides in the prior art.

Antibodies generated against the OLRCC1 5 receptor polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against OLRCC15 receptor polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with OLRCC15 receptor polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering OLRCC15 receptor polypeptide via a vector directing expression of OLRCC15 receptor polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a OLRCC15 receptor polypeptide wherein the composition comprises a OLRCC15 receptor polypeptide or OLRCC15 receptor gene. The vaccine formulation may further comprise a suitable carrier. Since OLRCC15 receptor polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art.

The dosage will depend on the specific activity of the vaccine and can be readily determined by routine experimentation.

Screening Assays

The OLRCC15 receptor polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

OLRCC15 receptor polypeptides are ubiquitous in the mammalian host and are responsible for many biological functions, including many pathologies. Accordingly, it is desirous to find compounds and drugs which stimulate OLRCC15 receptor on the one hand and which can inhibit the function of OLRCC15 receptor on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof. Such cells include cells from mammals, yeast, Drosophila or *E. coli*. Cells expressing the receptor (or cell membrane containing the expressed receptor) are then contacted with a test compound to observe binding, or stimulation or inhibition of a functional response.

One screening technique includes the use of cells which express the OLRCC15 receptor (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the receptor of the present invention is the yeast-based technology as described in U.S. Pat. No. 5,482,835.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential OLRCC 15 receptor antagonists include antibodies or, in some cases, oligonucleotides or proteins which are closely related to the ligand of the OLRCC15 receptor, e.g., a fragment of the ligand, or small molecules which bind to the receptor but do not elicit a response, so that the activity of the receptor is prevented.

Prophylactic and Therapeutic Methods

This invention provides methods of treating an abnormal conditions related to both an excess of and insufficient amounts of OLRCC15 receptor activity.

If the activity of OLRCC15 receptor is in excess, several approaches are available. One approach comprises administering to a subject an inhibitor compound (antagonist) as hereinabove described along with a pharmaceutically acceptable carrier in an amount effective to inhibit activation by blocking binding of ligands to the OLRCC15 receptor, or by inhibiting a second signal, and thereby alleviating the abnormal condition.

In another approach, soluble forms of OLRCC15 receptor polypeptides still capable of binding the ligand in competition with endogenous OLRCC15 receptor may be administered. Typical embodiments of such competitors comprise fragments of the OLRCC15 receptor polypeptide.

In still another approach, expression of the gene encoding endogenous OLRCC15 receptor can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of OLRCC15 receptor and its activity, several approaches are also available. One approach comprises administering to a subject a therapeutically effective amount of a compound which activates OLRCC15 receptor, i.e., an agonist as described above, in combination with a pharmaceutically acceptable carrier, to thereby alleviate the abnormal condition. Alternatively, gene therapy may be employed to effect the endogenous production of OLRCC15 receptor by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996).

Formulation and Administration

Peptides, such as the soluble form of OLRCC15 receptor polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection.

Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Cloning Method for the OLRCC15 receptor

The full length clone was obtained in the process of constructing a subtracted cDNA library from a human colorectal cancer tissue. The library was constructed using the Superscript Plasmid System for cDNA Synthesis and Plasmid Cloning (GIBCO BRL, Cat. 18248). The starting tissue was human colorectal cancer. A directional cDNA library was constructed using the vector pSport 1. Single-stranded DNA from the library was prepared utilizing standard procedures single-stranded DNA was subtracted with a driver consisting of photobiotinylated mRNA prepared from human normal colon tissue. The photobiotinylation and subtraction were performed using the Subtractor Kit (Invitrogen, Cat. 25-0004). After repairing the single-stranded circles, an electroporation was performed, and the clones obtained were plated. All of the clones obtained were analyzed by sequencing. The clone CC15 showed significant homology to olfactory receptor genes. The sequence of the insert was then determined.

Example 2

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectably in about 50% of the G418-resistant clones analyzed.

Example 3

Ligand bank for binding and functional assays

A bank of over 200 putative receptor ligands has been assembled for screening. The bank comprises: transmitters, hormones and chemokines known to act via a human seven transmembrane (7T) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 4
Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified.

Example 8
Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP flucuation are tested in vector control cells to determine if the response is unique to the transfected cells expressing receptor.

What is claimed is:

1. An isolated polynucleotide comprising a nucleotide sequence encoding at least one amino acid sequence selected from the group consisting of amino acids 1–20, 21–40, 41–60, 61–80, 81–100, and 101–316 from the amino acid sequence of SEQ ID NO:2.

2. The polynucleotide of claim 1 wherein said nucleotide sequence comprises the polynucleotide set forth in SEQ ID NO:1 encoding the amino acid sequence of SEQ ID NO:2.

3. The polynucleotide of claim 1 comprising the polynucleotide set forth in SEQ ID NO:1.

4. The isolated polynucleotide of claim 1 comprising a nucleotide sequence encoding the amino acid sequence set forth in SEQ ID NO:2.

5. The isolated polynucleotide of claim 1 wherein said polynucleotide is an RNA transcript of the entire length of SEQ ID NO:1.

6. The isolated polynucleotide of claim 1 wherein said polynucleotide is an RNA transcript of the entire coding region of SEQ ID NO:1.

7. An isolated polynucleotide which hybridizes under stringent hybridization conditions with a probe having a sequence encoding the polypeptide having the amino acid sequence of SEQ ID NO:2 wherein said stringent hybridization conditions comprise incubating at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA, and washing the filters in 0.1×SSC at about 65° C.

8. The isolated polynucleotide of claim 7 wherein the sequence of said probe comprises the polynucleotide sequence set forth in SEQ ID NO:1.

9. The isolated polynucleotide of any one of claims 1, 7, 4, or 8 which is DNA or RNA.

10. An isolated polynucleotide which is complementary to any one of the isolated polynucleotides of claims 1, 2, 3, 7, 4, or 8–6.

11. An expression system comprising a polynucleotide encoding a polypeptide comprising at least one amino acid sequence selected from the group consisting of amino acids 1–20, 21–40, 41–60, 61–80, 81–100, and 101–316 from the amino acid sequence of SEQ ID NO: 2.

12. A host cell comprising the expression system of claim 11.

13. A process for producing a polypeptide comprising at least one amino acid sequence selected from the group consisting of amino acids 1–20, 21–40, 41–60, 61–80, 81–100, and 101–316 from the amino acid sequence of SEQ ID NO:2 comprising culturing the host cell of claim 12 under conditions sufficient for the production of said polypeptide.

14. The process of claim 13 wherein said polypeptide is expressed at the surface of said cell.

15. The process of claim 13 which further includes recovering the polypeptide.

16. A polypeptide comprising at least one amino acid sequence selected from the group consisting of amino acids 1–20, 21–40, 41–60, 61–80, 81–100, and 101–316 from the amino acid sequence of SEQ ID NO:2 prepared by the process of claim 13.

17. A process for producing a cell which produces a polypeptide comprising at least one amino acid sequence selected from the group consisting of amino acids 1–20, 21–40, 41–60, 61–80, 81–100, and 101–316 from the amino acid sequence of SEQ ID NO:2 comprising transforming or transfecting a host cell with the expression system of claim 11 such that the host cell, under appropriate culture conditions, produces said polypeptide.

18. A cell produced by the process of claim 17.

19. An isolated polypeptide comprising at least one amino acid sequence selected from the group consisting of amino acids 1–20, 21–40, 41–60, 61–80, 81–100, and 101–316 from the amino acid sequence of SEQ ID NO:2.

20. The polypeptide of claim 19 comprising the amino acid sequence of SEQ ID NO: 2.

21. An expression system comprising a polynucleotide encoding a polypeptide comprising the amino acid sequence set forth in SEQ ID NO:2.

22. A host cell comprising the expression system of claim 21.

23. A process for producing a polypeptide comprising the amino acid sequence set forth in SEQ ID NO:2 comprising culturing the host cell of claim 22 under conditions sufficient for the production of said polypeptide.

24. The process of claim 23 wherein said polypeptide is expressed at the surface of said cell.

25. The process of claim 23 which further includes recovering said polypeptide.

26. A process for producing a cell which produces a polypeptide comprising the amino acid sequence set forth in SEQ ID NO:2 comprising transforming or transfecting a host cell with the expression system of claim 21 such that the host cell, under appropriate culture conditions, produces said polypeptide.

27. Cells produced by the process of claim 26.

* * * * *